United States Patent
Epshtein et al.

(10) Patent No.: US 9,308,259 B2
(45) Date of Patent: *Apr. 12, 2016

(54) MEDICINAL AGENT FOR TREATING FATNESS, DIABETES, AND DISEASES ASSOCIATED WITH IMPAIRED GLUCOSE TOLERANCE

(75) Inventors: Oleg Iliich Epshtein, Moscow (RU); Svetlana Alexandrovna Sergeeva, Moscow (RU)

(73) Assignee: Oleg Iliich Epshtein, Moscow (RU)

( * ) Notice: Subject to any disclaimer, the term of this patent is extended or adjusted under 35 U.S.C. 154(b) by 581 days.

This patent is subject to a terminal disclaimer.

(21) Appl. No.: 12/303,648

(22) PCT Filed: May 31, 2007

(86) PCT No.: PCT/RU2007/000288
§ 371 (c)(1),
(2), (4) Date: Sep. 28, 2010

(87) PCT Pub. No.: WO2007/149010
PCT Pub. Date: Dec. 27, 2007

(65) Prior Publication Data
US 2011/0008452 A1 Jan. 13, 2011

(30) Foreign Application Priority Data
Jun. 6, 2006 (RU) .................................. 2006119655
Jun. 6, 2006 (RU) .................................. 2006119658

(51) Int. Cl.
*A61K 41/00* (2006.01)
*C07K 16/28* (2006.01)
*A61K 39/00* (2006.01)

(52) U.S. Cl.
CPC ......... *A61K 41/0004* (2013.01); *C07K 16/2869* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 4,761,371 A | 8/1988 | Bell et al. | |
| 4,839,341 A | 6/1989 | Massey et al. | |
| 4,963,367 A | 10/1990 | Ecanow | |
| 5,683,712 A | 11/1997 | Cavazza | |
| 5,698,195 A | 12/1997 | Le et al. | |
| 5,856,111 A | 1/1999 | Ullrich et al. | |
| 5,861,266 A | 1/1999 | Ullrich et al. | |
| 5,879,677 A | 3/1999 | del Zoppo | |
| 6,007,824 A | 12/1999 | Duckett et al. | |
| 6,326,360 B1 | 12/2001 | Kanazawa et al. | |
| 6,803,452 B2 | 10/2004 | Schlessinger et al. | |
| 7,572,441 B2 | 8/2009 | Epshtein et al. | |
| 7,582,294 B2 | 9/2009 | Epshtein et al. | |
| 7,815,904 B2 * | 10/2010 | Epshtein et al. | 424/130.1 |
| 8,617,555 B2 * | 12/2013 | Epshtein | 424/158.1 |
| 2003/0099636 A1 | 5/2003 | Epshtein et al. | |
| 2004/0198648 A1 | 10/2004 | Grunberger et al. | |
| 2006/0165697 A1 | 7/2006 | Epshtein et al. | |
| 2007/0123518 A1 | 5/2007 | Epshtein | |
| 2009/0148521 A1 | 6/2009 | Epstehin | |

FOREIGN PATENT DOCUMENTS

| | | |
|---|---|---|
| CA | 2654408 A1 | 12/2007 |
| EP | 0652014 A1 | 5/1995 |
| EP | 0687466 A1 | 12/1995 |
| EP | 1 295 606 A1 | 3/2003 |
| EP | 1997481 A1 | 12/2008 |
| RU | 2007989 C1 | 2/1994 |
| RU | 2033784 C1 | 4/1995 |
| RU | 2104032 C1 | 2/1998 |
| RU | 2122858 C1 | 12/1998 |
| RU | 2137483 C1 | 9/1999 |
| RU | 2144370 C1 | 1/2000 |
| RU | 98109384 A | 3/2000 |
| RU | 2192882 C1 | 11/2002 |
| RU | 2199345 C1 | 2/2003 |
| WO | 9412213 A1 | 6/1994 |
| WO | 9728776 A1 | 8/1997 |
| WO | 97/32595 A1 | 9/1997 |
| WO | 9814161 A1 | 4/1998 |
| WO | 0105371 A1 | 1/2001 |
| WO | 2004012765 A1 | 2/2004 |

OTHER PUBLICATIONS

Giorgino et al., J. Clin. Invest., 1993, 91: 2020-2030.*
Mayo Foundation for Medical Education and Research, 2012, accessed at mayoclinic.com/health/type-1-diabetes/DS00329 on Sep. 13, 2012.*

(Continued)

*Primary Examiner* — Ilia Ouspenski
(74) *Attorney, Agent, or Firm* — Pergament & Cepeda LLP; Milagros A. Cepeda; Edward D. Pergament

(57) ABSTRACT

The inventive medicinal agent comprises antibodies against beta-subunit of insulin receptor in an activated form produced by means of repeated serial dilution and an external action performed according to homeopathic technology. The inventive method for producing a solid medicinal formulation for perorally treating fatness, diabetes, and other diseases associated with impaired glucose tolerance, consists in mixing the effective amount of carrier, which is showered in a fluidized layer by a water-alcohol dilution of antibodies in the form active against the beta-subunit of the insulin receptor produced by combining the repeated serial dilution, thereby reducing the concentration of antibodies, and an external action according to homeopathic technology, and is dried at a temperature equal to or less than 35° C., with pharmaceutically acceptable additives and in subsequently pelleting the mixture thus obtained by means of direct dry compression.

5 Claims, No Drawings

(56) References Cited

OTHER PUBLICATIONS

Aly et al., Am. J. Therapeutics (2005) 12: 481-490.*
Pillemer et al., J. Rheumatol. (2003) 30: 41-43.*
Ernst, 2005, Trends in Pharmacological Science, 26: 547-548.*
Declaration filed on Oct. 28, 2008 in U.S. Appl. No. 10/522,652, 2 pages.*
Declaration filed on Sep. 29, 2008 in U.S. Appl. No. 10/522,653, 2 pages.*
Alexandrova et al., "An Experience of Application of Potentiated Compounds for Jugulation of Alcohol Abstinent Syndrome and Opiate Abstinent Syndrome," Bull of Siberian Branch of RAMS, No. 1 (91), 1999.
Beregovoy et al., On influence of various Dilutions of Monoclonal Antibodies 5F5-B6 on the Formation of Long-Term Post-Tetanic Potentiation in Survived Hippocampal Slices, Bull of Siberian Branch of RAMS No. 1 (91), 1999.
Davenas et al., Nature, 1988, 333: 816-818.
Epshtein et al. May 1999, Bulletin of Experimental Biology and Medicine, vol. 5: 493-495.
Frimel, G., ed., "Immunological Methods," Medicina Publishing House, 1987, pp. 9-33.
Gaevy, M.D. et al., "Osnovy klinicheskoi farmakologii I farmakoterapii," Moscow, Aliyans-B, 2002, pp. 42-44.
Goldacre (2007) Lancet 370: 1672-1673.
Grigoriev M. Yu. et al., "K probleme ispolzovaniya potentsirovannykh organnykh preparatov," Lechebno-profilakticheskaja Rabota Dlya Meditsinskikh Organizatsij V Ugolnoj Promyshlennosti, vyp. 8, 1989, izd. Tsniehi ugol (Moscow), pp. 163-165.
International Search Report from International Application No. PCT/RU02/00367, filed Aug. 2, 2002, mailed on Dec. 19, 2002.
International Search Report from International Application No. PCT/RU01/00239, filed Jun. 19, 2001, mailed on Sep. 20, 2001.
International Search Report from International Application No. PCT/RU02/00365, filed Aug. 2, 2002, mailed on Dec. 5, 2002.
International Search Report from International Application No. PCT/RU06/00237, filed May 16, 2006, mailed on Nov. 23, 2006.
International Search Report from International Application No. PCT/RU04/000374, filed Sep. 27, 2004, mailed on Feb. 10, 2005.
International Search Report from International Application No. PCT/RU02/00368, filed Aug. 2, 2002, mailed on Dec. 5, 2002.
International Search Report from International Application No. PCT/RU02/00369, filed Aug. 2, 2002, mailed on Dec. 19, 2002.
International Search Report from International Application No. PCT/RU97/00026, filed Feb. 10, 1997, mailed on Apr. 8, 1997.
Ivaniushkin, A. Ja., "Gomeopatiya i sovremennaya meditsina," Vestnik Akademii Meditsinskikh Nauk SSSR, 4, 1988, izd. "Meditsina" (Moscow), pp. 76-82.
Janeway et al. Immunobiology, 1997, 3rd edition, Garland Publishing Inc., pp. 3:1-3:11.
Linde et al., 1997, Lancet, vol. 350: 834-43.
Register of Pharmaceuticals of Russia, Encyclopedia of Pharmaceuticals (in Russian), Moscow, 2000, pp. 358-359.
Register of Pharmaceuticals of Russia, Encyclopedia of Pharmaceuticals (in Russian), Moscow, 2001, pp. 788-789.
Schwab, V., "Homeopathic Pharmaceutical Agents. A manual on description and preparation," Moscow, 1967, pp. 12-38.
Schwabe, W., "German Homeopathic pharmacopoeia (Homeopathisches Arzneibuch)," Stuttgart, Translation of the 5th Supplement (1991) to the 1978 edition.
Shang et al., 2005, Lancet, vol. 366: 726-32.
Stefani, D. V. et al., "Immunologiya i immunopatologiya detskogo vozrasta," Moscow, Meditsina, 1996, pp. 28, 29, 358-359.
Vasiliev, Yu, V. et al., "Gomeopatiya: vozrozhdenie traditsionnioy meditsinskoj shkoly," Vestnik Rossijkoj Akademii Nauk, 10, 1992, izd. "Nauka" (Moscow), pp. 145-148.
Vyazov, O.L., Laboratory Methods of Studies in Non-Infection Immunology (in Russian)m Moscow, Meditsina, 1968.
Third Office Action issued on Aug. 6, 2014 for corresponding Chinese Patent Application No. 200780028298.5.
Vickers, "Clinical trials of homeopathy and placebo: Analysis of a scientific debate", Journal of Alternative and Complementary Medicine, Feb. 1, 2000, vol. 6, pp. 49-56, New York, NY.
Jonas, et al., "A critical overview of homeopathy", Annals of Internal Medicine, Mar. 4, 2003, pp. 393-399, vol. 138, No. 5, New York, NY.
Chueshov, et al., "Drug manufacturing process", 1999, vol. 2, Kharkov, Ukraine.
Sander, et al., "Technology and equipment of galenical drugs production", 1956, pp. 482-483, State Medical Books Publishing House, Leningrad, Russia.
Burgasov, "Guides on vaccines and serological issues", 1978, pp. 327, Moscow, Soviet Union.
Voronova, et al., "Cytogenic effects of antibodies to y-interferon in ultralow doses", Bulletin of Experimental Biology and Medicine, 2005, pp. 66-67, Plenum Publishing Corporation.
Romanova, et al., "Neuroprotective activity of propoten in rats with experimental local photothrombosis of the prefrontal cortex", Bulletin of Experimental Biology and Medicine, 2005, pp. 404-407, vol. 139, No. 4, Springer Sciences Business Media, Inc.
Bokhan, et al., "Comparative efficiency of proptoten-100 during the therapy of patients with alcoholism in the stage of therapeutic remission", Pharmacology of Ultralow Doses, p. 171, Institute of Mental Health Tomsk Research Center, Siberian Division of the Russian Academy of Medical Sciences.
Epshtein, et al., "Dose-dependent effects and specificity of action of antibodies to endogenous regulators in ultralow doses", 2004, pp. 460-462, Bulletin of Experimental Biology and Medicine, Pharmacology and Toxicology, Plenum Publishing Corporation.
Krylova, et al., "Antiulcer activity of ultralow doses of antibodies to histamine under experimental conditions", Bulletin of Experimental Biology and Medicine, 2003, pp. 80-82, Plenum Publishing Corporation.
Spasov, et al., "Study of antidiabetic activity of a new ultralow-does antibody preparation on the model of streptozotocin in diabetes in rats". Bulletin of Experimental Biology and Medicine, Pharmacology and Toxicology, vol. 144, No. 1, pp. 46-48, Springer Business Media Inc.
Dugina, et al., "A randomized, open-label, comparative, 6 month trial of oral ultra-low doses of antibodies to tumor necrosis factor and diclofenac in rheumatoid arthritis", Int. J. Tissue React, 2005, pp. 15-21, Bioscience Ediprint Inc.
Beregovoi, et al., "Effect of antibodies to morphine in ultralow doses of induction of long-term potentiation in hippocampal slices from rats with chronic morphine dependence", Bulletin of Experimental Biology and Medicine, 2003, pp. 26-28, Plenum Publishing Corporation.
Veltishev, et al., "Immunological and immunopathology of childer", Guideline for Physicians.
Markel, et al., "Hypotensive activity of ultralow doses of antibodies to factors involved in the regulation of vascular tone", Pharmacology of Ultralow Doses, 2003, pp. 57-59, Plenum Publishing Corporation.
Epshtein, et al., "Improvement of memory by means of ultra-low doses of antibodies to S-100B antigen" Advance Access Publication, 2006, pp. 541-545, Institute of Molecular Biology and Biphysics, Siberian Department of Russian Academy of Medical Sciences, Novosibrisk, Russia.
Petrov, et al., "Open randomized parallel clinical study of the efficacy and safety of various dosing regimen for ultra-low dose antibodies to insulin receptor beta-subunit C-terminal fragment in type 2 diabetes mellitus patients, with additional control group, receiving glibenclamide" 2008, pp. 1-55, Report # A11071251-30.CD, Materia Medica Holding Research and Manufacturing Company, Moscow Russia.
Mikhailovitch, "Expert report with regard to case No. 2-2954/2009", Oct. 2009, pp. 1-9, Central District of Chelyabinks, Chelyabinsk, Russia.
Beregovoi, et al, "On the issue of the effect of various dilutions of monoclanal antibodies 5F5-B6 on formation of the long-term post-tetanic potentiation in surviving hippocampal sections", Bulletin of the Siberian Department of Russian Academy of Medical Sciences 1999, No. 1(91), Moscow, Russia.

(56) References Cited

OTHER PUBLICATIONS

Uchida, et al., "The mechanism of insulin receptor activation upon insulin binding", Nippon Rinsho, 2002, vol. 60, Special Issue No. 7, pp. 234-239.

Notice of Reasons for Rejection issued by the Japanese Patent Office on Jul. 31, 2012 for corresponding Japanese Patent Application No. 2009-514226.

* cited by examiner

```
SEQUENCE LISTING

<160> NUMBER OF SEQ ID NOS: 1

<210> SEQ ID NO 1
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /note="InsR beta subunit P06213 SwissProt aa 1366-1392"
      /organism="Homo sapiens"

<400> SEQUENCE: 1

Gly Gly Lys Lys Asn Gly Arg Ile Leu Thr Leu Pro Arg Ser Asn Pro
1               5                   10                  15

Ser
```

MEDICINAL AGENT FOR TREATING FATNESS, DIABETES, AND DISEASES ASSOCIATED WITH IMPAIRED GLUCOSE TOLERANCE

FIELD OF THE INVENTION

The invention concerns the field of medicine and may be used for effective treatment and prevention of obesity, diabetes mellitus and other diseases associated with impaired glucose tolerance.

PRIOR ART

Based on the prior knowledge, the medicinal drug (medication) for the treatment of obesity, diabetes mellitus and other diseases associated with impaired glucose tolerance is known (e.g. see Register of Medicinal Drugs of Russia "Encyclopedia of the Drugs", 14th edition, Moscow, Register of Medicinal Drugs (RMD), 2006, pp. 223-226. pp. 329-332, P. 510, P. 731).

However, the use of such drugs does not provide stable effect, particularly due to the tolerance to them; besides, it may be accompanied by side effects.

A method of obtaining solid oral form of the drug including pressing of dry ground components containing the active substance and pharmaceutically acceptable additives (RU 2203054 C2, A61K9/20, 2003) is also known.

However, such method is not suitable for manufacturing of medicinal drugs containing antibodies as they are made in liquid dosage form for injections and are administered parenterally in order to provide bioavailability.

DISCLOSURE OF THE INVENTION

The invention is intended for development of an effective antibody-based drug used for peroral treatment of obesity, diabetes mellitus and other diseases associated with impaired glucose tolerance with no side effects and the method of its production in solid dosage form.

Solution of the task is ensured by the fact that a peroral drug for the treatment of diabetes mellitus and other diseases associated with impaired glucose tolerance, according to the invention contains antibodies to beta-subunit of the insulin receptor in activated form obtained by multiple successive dilution and external action in accordance with homeopathic technology.

At that the medicinal drug (medication) contains monoclonal, polyclonal, recombinant, immune or natural antibodies to beta-subunit of the insulin receptor in activated form.

Furthermore, the medicinal drug contains mixture of various homeopathic dilutions of antibodies to beta-subunit of the insulin receptor in activated form.

Solution of the task is also ensured by the fact that method of production of solid oral form for the treatment of diabetes mellitus and other diseases associated with impaired glucose tolerance according to the invention includes mixing of effective amount of carrier irrigated in a fluidized bed by combination of aqueous-alcohol dilution of antibodies to beta-subunit of the insulin receptor in activated form obtained by combining multiple successive dilution-reduction in antibody concentration and external action according to homeopathic technology and dried at temperature not exceeding 35ϵ C., with pharmaceutically acceptable additives and subsequent pelletization of mixture by direct dry pressing.

Lactose with particle size of 150-250 μm is used as a carrier for this method of obtaining solid medicinal form.

The experiments confirmed that the medicinal drug administered orally and prepared by multiple successive dilution and external action, mainly according to homeopathic technology, of antibodies to beta-subunit of the insulin receptor provides modifying effect on physiological processes mediated by beta-subunit of the insulin receptor, particularly on impaired glucose metabolism specific for obesity, diabetes mellitus, etc ensuring therapeutic efficacy of the medicinal drug subject to patent application.

The medicinal drug prepared in accordance with the invention is a novel antibody-based pharmaceutical drug characterized by specific pharmacological activity, high efficacy; absence of side effects, ecological purity and low cost.

EMBODIMENTS OF THE INVENTION

The medicinal drug is prepared in the following way.

A fragment of beta-subunit of human insulin receptor (No. P06213 in the Swissprot database of protein sequences, ID No. 33112647) is used as immunogen for immunization of laboratory animals in order to produce polyclonal immune antibodies or in hybridoma technology for production of recombinant monoclonal and polyclonal antibodies. The fragment is SEQ ID NO: 1. The obtained antibodies are purified by affinity chromatography. Mixture of various fragments may be used as immunogen.

SEQ ID NO. 1:

Gly Gly Lys Lys Asn Gly Arg Ile Lue Thr Leu Pro Arg Ser Asn Pro Ser
1                5                    10                   15

The method of immune and monoclonal antibodies is described, for example, in the book Immunological methods/ Edited by G. Frimel, Moscow, Medicina, 1987, pp. 9-33.

Method of natural antibodies production is described in the book "Natural antibodies to low-molecular compounds". M. A. Myagkova, Moscow, MGUL, 2001 (ISBN 5-8135-0058-8), pp. 70-114.

Method of recombinant antibodies production is described in the article by Laffly E., Sodoyer R. Hum. Antibodies. Monoclonal and recombinant antibodies, 30 years after.—2005—Vol. 14.—N 1-2. pp. 33-55.

Isolated antibodies are subjected to successive and multiple dilution-reducing their concentration and subjecting them to external, usually mechanical treatment e.g. according to homeopathic technology of potentiating (see Homeopathic medicinal drugs. Guidelines on description and manufacturing. V. Shvabe, Moscow, 1967, pp. 12-38; or G. Keller, Homeopathy, Moscow, Medicina, 2000, part 1, pp. 37-40). At that steady concentration reduction is performed by successive dilution of 1 part by volume of the starting substance (antibodies) in 9 parts by volume (for decimal D dilution) or in 99 parts by volume for centesimal C dilution) or in 999 parts by volume for millesimal dilution) of neutral solvent—distilled water and/or 70% ethyl alcohol with multiple vertical shaking of each dilution obtained and using mainly separate containers for each subsequent dilution until the required dilution is achieved.

Ultrasound, electromagnetic or other physical influence can be used for external treatment in the process of concentration reduction.

To improve therapeutic effect of the drug mixture of various homeopathic dilutions may be used.

The obtained dilution in the form of aqueous or alcohol solution may be used as a liquid dosage form for peroral administration into the body (in the form of drops) or for subsequent preparation of solid oral form.

At the stage of producing of solid dosage form for peroral therapy in the fluidized bed, e.g. of Huttlin Pilotlab type manufactured by Huttlin GmbH, irrigation in fluidized bed of granules of neutral substance—lactose (milk sugar) with particle size of 150-250 µm prepared according to the aforementioned technology using aqueous-alcohol dilution (preferably, centesimal) of the activated form of antibodies to beta-subunit of the insulin receptor with simultaneous drying at temperature not exceeding 35∈ C. is conducted.

Calculated amount of the prepared "saturated" lactose is loaded into the mixer and mixed with microcrystalline cellulose administered at 10.0-15.0 mass % of the total loading weight. Then "nonsaturated" lactose is added to mixture (to reduce price and slightly facilitate and accelerate technological process without reducing therapeutic efficacy by means of reduction of pharmaceutical substance concentration in the tablet if required: aqueous-alcohol dilution of activated form of antibodies) in 30-80 mass % of the total loading weight and magnesium stearate at 0.8-1.2 mass % of the total loading weight and they are stirred evenly.

Obtained dry homogeneous mixture is supplied to the pelletizing machine, for example, tablet-press Korsch-XL 400, to form round 150-500 mg tablets using direct dry pressing.

Example 1

Patient K., 62 years old, obesity of $3^{rd}$ degree (body mass index 36) has long been suffering from insulin-independent diabetes. He takes sugar-reducing drugs (for the last months glibenclamide at a dose of 10 mg/day). On the background of glibenclamide intake hypoglycemia periodically developed, the patient complained of headache, dizziness, etc. Glibenclamide was assigned in combination with polyclonal rabbit antibodies to beta-subunit of the insulin receptor (mixture of homeopathic dilutions C12+C30+C200) at a dose of 5 drops per os twice a day. No cases of hypoglycemia were registered during 4-week treatment, glucose tolerance was normalized. After 1.5-month treatment the patient stopped taking glibenclamide, glucose level was within the normal range. Body mass index reduced up to 33. Continuation of the antibody-based drug therapy was recommended.

Example 2

Patient M., 46 years old, complained of rapid fatigability. The examination revealed obesity of $2^{nd}$ degree. Recommendations: 1 tablet "saturated" with potentiated antibodies—homeopathic dilution C30 of monoclonal antibodies to beta-subunit of the insulin receptor—three times per day. Six-week drug administration resulted in weight reduction by 7% and improvement of physical tolerance.

Example 3

Patient K., 36 years old, complained of insomnia, increased food intake, dyspnea. The examination showed obesity of $3^{rd}$ degree, body mass index 41 kg/m. The intake of the drug in tablet form containing antibodies to beta-subunit of the insulin receptor (mixture of homeopathic dilutions C12+C30+C200)—2 tablets twice per day—allowed to normalize appetite and reduce BMI up to 36 kg/m$^2$ within 4 weeks.

Example 4

Patient D., 43 years old, underwent a course of obesity treatment. Complained of ineffective dietary treatment. Five-week administration of the drug containing antibodies to beta-subunit of the insulin receptor in homeopathic dilution C200 at a dose of 1 tablet 4 times/day allowed to reduce the patient's body weight by 10%.

Example 5

Antidiabetic activity of aqueous solution of the drug containing activated form of rabbit polyclonal antibodies to beta-subunit of the insulin receptor (mixture of homeopathic dilutions C12+C30+C200) was studied in the model of outbred male rats with streptozotocin-induced diabetes. The drug was administered intragastrically at a dose of 2.5 mL/kg per rat for 50 days. Insulin (Actrapid HM at 12 units/kg/day subcutaneously) and glibenclamide (MP Biomedical at a dose of 8 mg/kg/day per os) were used as reference drugs. The results showed significant activity of the drug exceeding the one of the reference drugs. On day 7 of the treatment blood and urine glucose levels were significantly reduced, glucose tolerance was normalized. On day 14 these parameters almost reached the normal values. The drug effect persisted for all 50 days of the treatment. Insulin and glibenclamid administration provided antidiabetic effect of various degrees on aforementioned parameters; however, the effect intensity was significantly lower than that in the group of animals receiving activated form of antibodies to beta-subunit of the insulin receptor.

Example 6

Patient M., 15 years old, diagnosis of 1 type diabetes mellitus, disease duration—7 years. Due to reduced efficacy of insulin therapy (long-term insulin drugs) the following recommendations were made: activated form of monoclonal murine antibodies to beta-subunit of human insulin receptor (mixture of homeopathic dilutions C12+C30+C200)—1 tablet for dissolution in the mouth 2 times/day. After 2-week treatment insulin therapy efficacy was significantly improved; due to this insulin dose was reduced from 0.5 units/kg/day to 0.3 units/kg/day. Further (in 3 months) the dose of insulin was reduced up to 0.1 units/kg/day.

Example 7

Patient S., 53 years old, BMI 30, has been suffering from insulin-independent diabetes mellitus for 8 years, the syndrome of diabetic foot is present. The great toe of the right leg was amputated one year ago. The patient complained of non-healing (1.5 months) ulcers on the right leg in the area of amputated toe. The patient was assigned with rabbit polyclonal antibodies to beta-subunit of human insulin receptor (mixture of homeopathic dilution D6+C30+C50) at a dose of 1 tablet once daily (the tablet has to be dissolved in the mouth). Three weeks later healing of ulcerative process was registered, and insulin tolerance was reduced. The patient went on taking the drug for 3 months that resulted in stabilization of glycemia. The patient noted significant body weight loss (IMT reduced to 28).

Example 8

Patient Z., 72 years old, complained of subcompensated insulin-independent diabetes mellitus. Recombinant human antibodies to beta-subunit of human insulin receptor in homeopathic dilution C30 at a dose of 1 tablet per os 3 times/day were recommended. Seven days later hyperglycemia was reduced, two weeks later glucose level was normalized, and physical tolerance was improved.

Example 9

Patient D., 8 years old, diagnosis of I type diabetes mellitus since 5 years old. The course of the disease quickly progresses. On admission glycemia was 20 mmol/l; the patient received human recombinant insulin at a dose of 30 units/day. Intake of polyclonal rabbit antibodies to C-terminal fragment of beta-subunit of the insulin receptor (mixture of homeopathic dilutions C12+C30+C200) at a dose of 2 tablets 2 times/day (tablet has to be dissolved in the mouth) was recommended; insulin administration continued at the same dose. In 3 days of the treatment glycemia reduced to 15.5 mmol/l; in 2 weeks of the treatment the level of glucose normalized and remained stable. The improvement achieved made it possible to reduce insulin dose in 3 months after the onset of the treatment up to 10 units/day. It was recommended to continue the treatment.

Example 10

Patient A, 51 years old. For a long time she has been observed by endocrinologist for decompensated 1 type diabetes mellitus with signs of nephropathy, neuropathy, skin lesions and retinopathy. In addition to insulinotherapy administration of ultra low doses of goat polyclonal antibodies to beta-subunit of the insulin receptor (mixture of homeopathic dilutions C12+C30+C200) at a dose of 1 tablet 3 times/day (the tablet has to be dissolved in the mouth) was assigned. Two weeks later skin itching and proteinuria (from 0.4 g/L to 0.1 g/L) were significantly reduced, skin ulcers on the legs were almost healed. The patient noted improved general state, reduced dyspnea, increased ability to work. Prolongation of the treatment was recommended in order to reduce the dosage of insulin injections.

The invention claimed is:

1. A medication for peroral treatment of diabetes mellitus, impaired glucose tolerance and obesity associated with diabetes mellitus or impaired glucose tolerance, comprising a homeopathically potentized form of at least one antibody to the beta-subunit of the insulin receptor.

2. The medication according to claim 1 wherein said at least one antibody is a monoclonal, polyclonal, recombinant, immune or natural antibody.

3. The medication according to claim 1 wherein said homeopathically potentised form of antibody comprises mixture of various homeopathic dilutions.

4. A method for producing a solid oral dosage form of claim 1, the method comprising:
   providing a carrier;
   irrigating said carrier with a homeopathically potentized form of at least one antibody to the beta-subunit of the insulin receptor;
   mixing said carrier with pharmaceutically acceptable additives;
   drying said carrier at a temperature not exceeding 35° C.; and
   forming said irrigated carrier into said oral dosage form by direct dry pressing.

5. The method according to claim 4 wherein the carrier is lactose with a particle size of from about 150 μm to about 250 μm.

* * * * *